United States Patent
Thomas

(10) Patent No.: US 9,826,983 B2
(45) Date of Patent: Nov. 28, 2017

(54) MEDICAL DEVICE FOR CONTROLLED NAIL PENETRATION

(71) Applicant: Rolf Lewis Thomas, Worthing (GB)

(72) Inventor: Rolf Lewis Thomas, Worthing (GB)

( * ) Notice: Subject to any disclaimer, the term of this patent is extended or adjusted under 35 U.S.C. 154(b) by 414 days.

(21) Appl. No.: 14/320,694

(22) Filed: Jul. 1, 2014

(65) Prior Publication Data

US 2014/0371751 A1    Dec. 18, 2014

Related U.S. Application Data

(63) Continuation of application No. PCT/GB2012/053174, filed on Dec. 18, 2012.

(30) Foreign Application Priority Data

Jan. 1, 2012  (GB) .................................... 1200005

(51) Int. Cl.
*A61B 17/54*    (2006.01)
*A61B 17/16*    (2006.01)
*A61B 90/00*    (2016.01)

(52) U.S. Cl.
CPC ...... *A61B 17/1626* (2013.01); *A61B 17/1662* (2013.01); *A61B 17/54* (2013.01); *A61B 90/03* (2016.02); *A61B 2090/064* (2016.02)

(58) Field of Classification Search
CPC .................................................. A61B 17/54
See application file for complete search history.

(56) References Cited

U.S. PATENT DOCUMENTS

| | | | | |
|---|---|---|---|---|
| 3,583,821 A * | 6/1971 | Shaub | ................ | B23Q 11/0053 144/252.1 |
| 3,766,923 A * | 10/1973 | Boretos | ................... | A61B 17/32 606/28 |
| 4,180,058 A * | 12/1979 | Brem | ...................... | A61B 17/54 128/898 |
| 4,267,841 A * | 5/1981 | Fraser | ..................... | A61B 17/54 606/180 |
| 5,645,554 A * | 7/1997 | Hugh | ................. | A61B 17/1662 606/172 |
| 5,795,314 A * | 8/1998 | Berenstein | ............. | A61H 35/00 132/74.5 |

(Continued)

OTHER PUBLICATIONS

Futek Advanced Sensor Technology, Inc. http://www.futek.com/product.aspx?t=torque&cat=rs Available at least Jul. 21, 2006.*

(Continued)

*Primary Examiner* — David Bates
(74) *Attorney, Agent, or Firm* — Anderson Gorecki LLP

(57) ABSTRACT

The present invention relates to a device for penetrating human nails as a part of treatment for Onychomycosis, commonly known as fungal nail. The device comprises a reusable electromechanical system and a single use cutting component. The electromechanical system incorporates an electrical motor and drive train to advance the cutting component through the nail. The electromechanical system also incorporates sensors for measuring the cutting resistance for the purpose of preventing the cutting device from overrunning into the nail bed. The device can be used to penetrate the nail in a controlled manner which will create a portal through the nail without penetrating the nail bed below the nail.

17 Claims, 8 Drawing Sheets

(56) References Cited

U.S. PATENT DOCUMENTS

| | | | | |
|---|---|---|---|---|
| 6,015,418 | A * | 1/2000 | Wymond | A61B 17/34 606/167 |
| 6,264,628 | B1 | 7/2001 | Feldman | |
| 6,572,580 | B2 * | 6/2003 | Feldman | A01N 25/34 132/75.4 |
| 7,848,799 | B2 * | 12/2010 | Herndon | A61B 5/053 600/547 |
| 8,150,505 | B2 * | 4/2012 | Herndon | A61B 5/063 600/547 |
| 9,345,487 | B2 * | 5/2016 | Herndon | A61B 5/053 |
| 9,504,849 | B2 * | 11/2016 | Yoo | A61N 5/0624 |
| 2002/0085891 | A1 * | 7/2002 | Moore | B23B 27/045 408/230 |
| 2006/0041241 | A1 * | 2/2006 | Herndon | A61B 5/053 604/500 |
| 2006/0225757 | A1 * | 10/2006 | Jamison | A45D 29/05 132/73.6 |
| 2007/0104664 | A1 * | 5/2007 | Maltezos | A61N 5/0616 424/61 |
| 2009/0245956 | A1 * | 10/2009 | Apkarian | A61B 17/1626 408/1 R |
| 2010/0145373 | A1 * | 6/2010 | Alon | A61B 17/1662 606/169 |
| 2011/0020084 | A1 | 1/2011 | Brett et al. | |
| 2011/0046626 | A1 | 2/2011 | Herndon | |
| 2011/0144564 | A1 * | 6/2011 | Hennings | A61B 18/203 604/20 |
| 2011/0243673 | A1 | 10/2011 | Svagr | |
| 2011/0301628 | A1 * | 12/2011 | Gross | A45D 31/00 606/169 |
| 2014/0236203 | A1 * | 8/2014 | Dolev | A61B 17/3209 606/180 |
| 2014/0358171 | A1 * | 12/2014 | Dolev | A61B 17/3209 606/180 |
| 2015/0119912 | A1 * | 4/2015 | Dolev | A61B 17/3209 606/167 |
| 2016/0175612 | A1 * | 6/2016 | Kazic | A61N 5/0624 606/3 |

OTHER PUBLICATIONS

International Search Report from corresponding PCT application PCT/GB2012/053174.

* cited by examiner

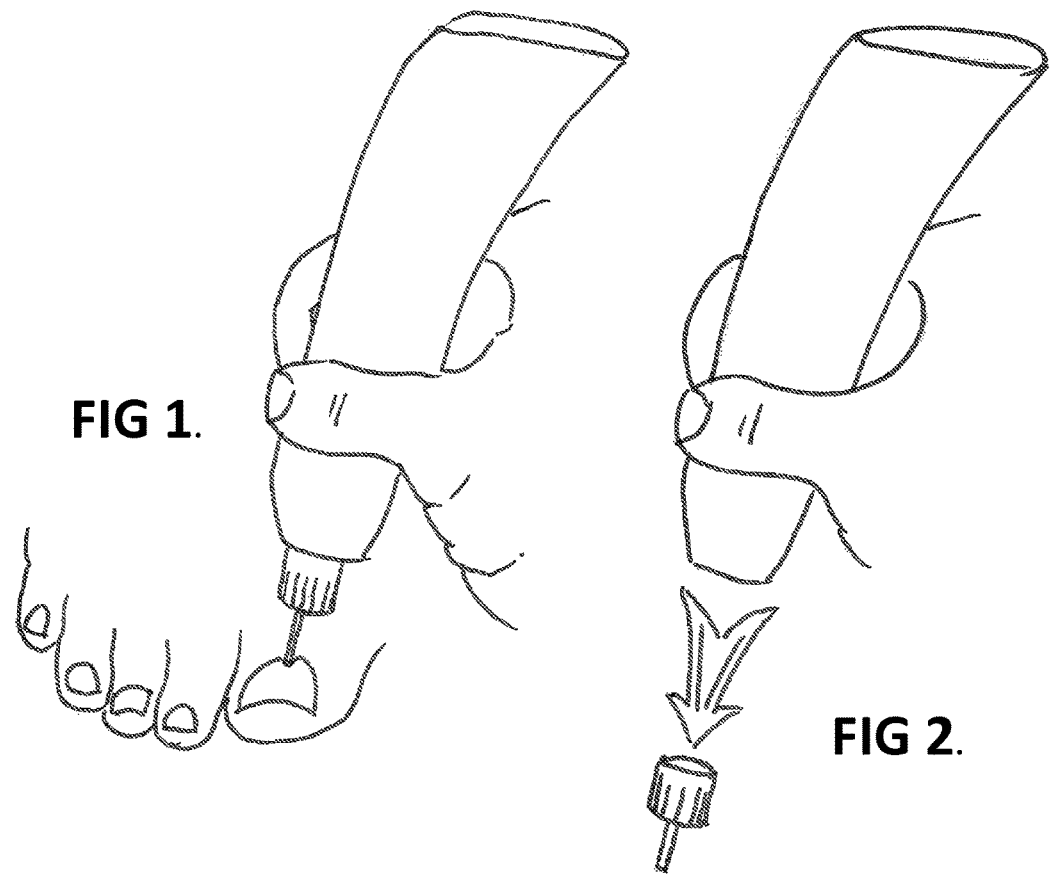
FIG 1.
FIG 2.
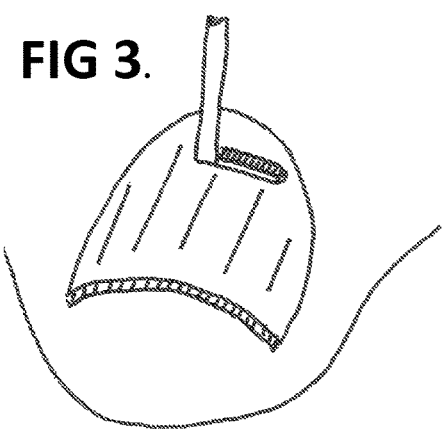
FIG 3.

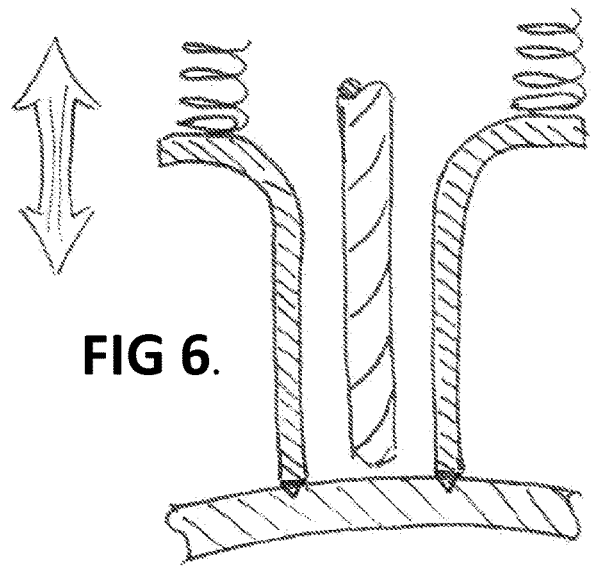
FIG 6.
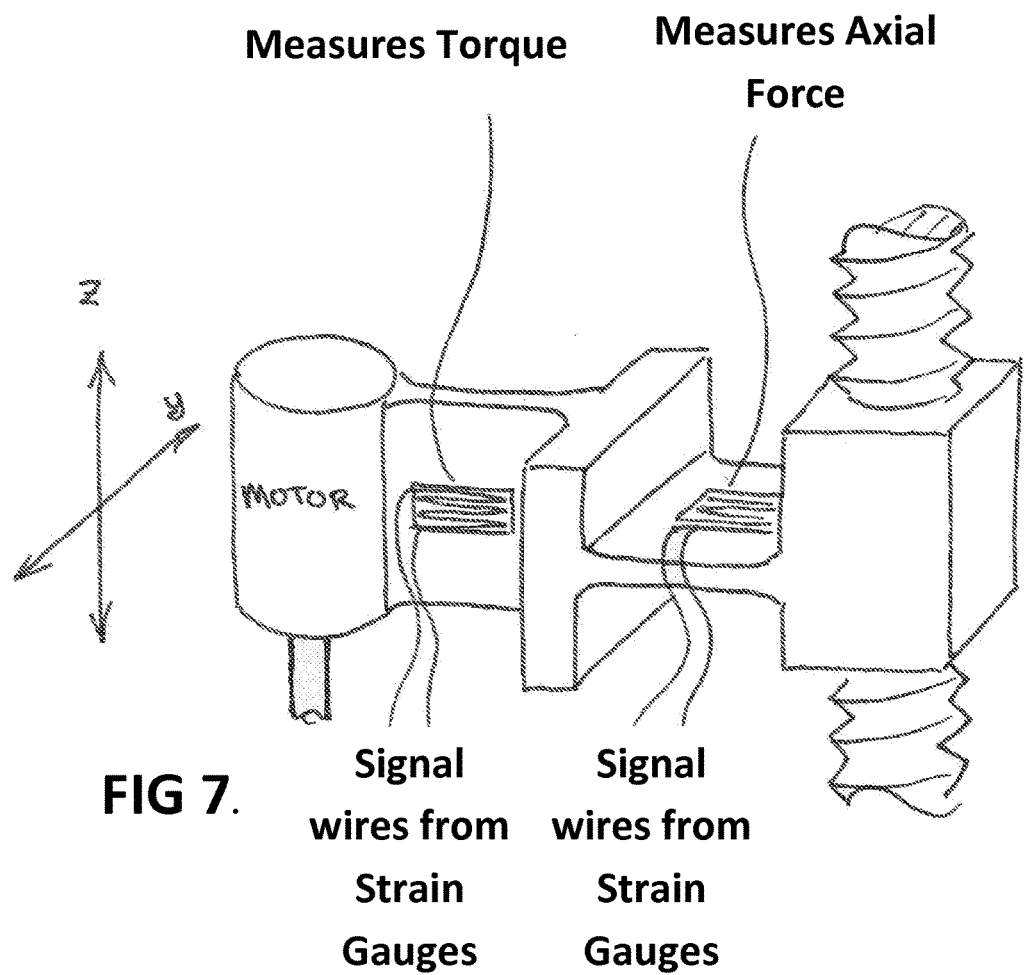
Measures Torque   Measures Axial Force
FIG 7.   Signal wires from Strain Gauges   Signal wires from Strain Gauges

FIG 8.
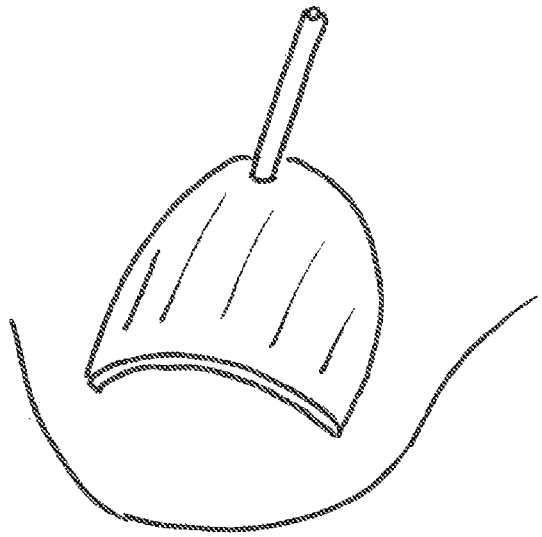
1. 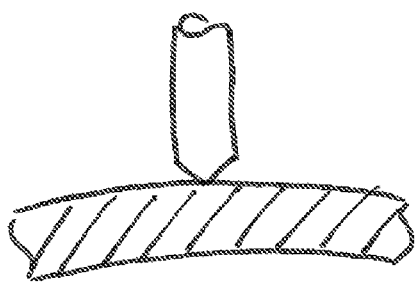
2. 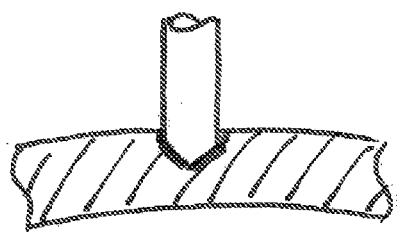
3. 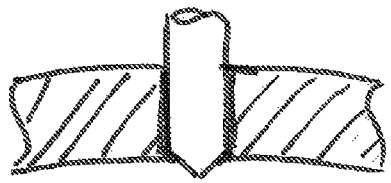

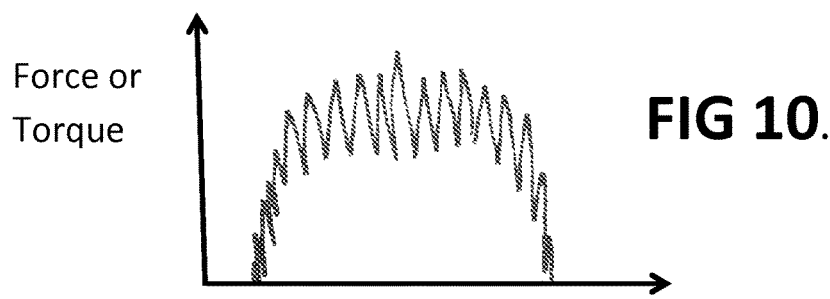
FIG 10.
a. Force or Torque
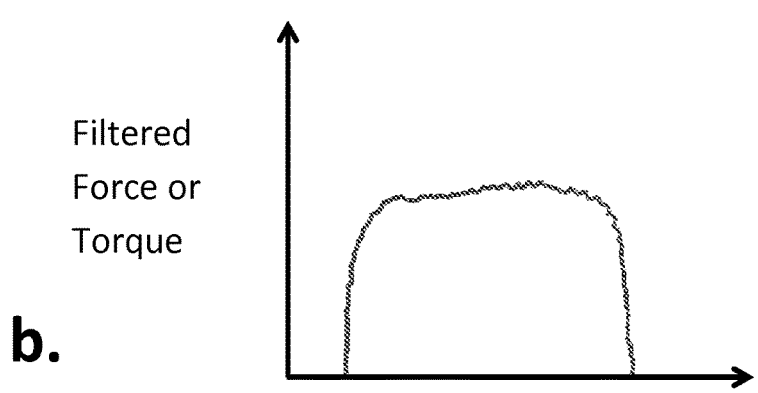
b. Filtered Force or Torque
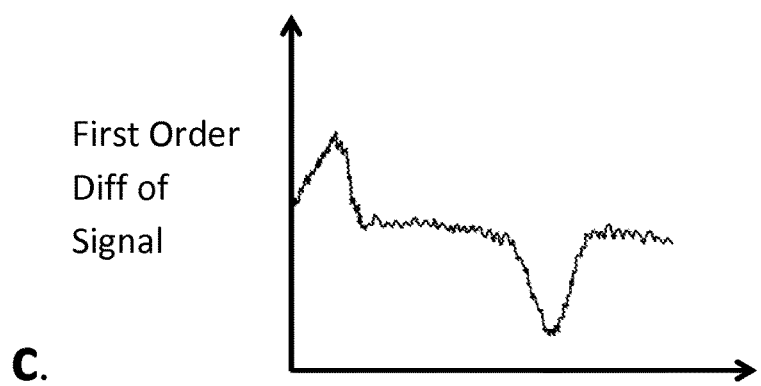
c. First Order Diff of Signal
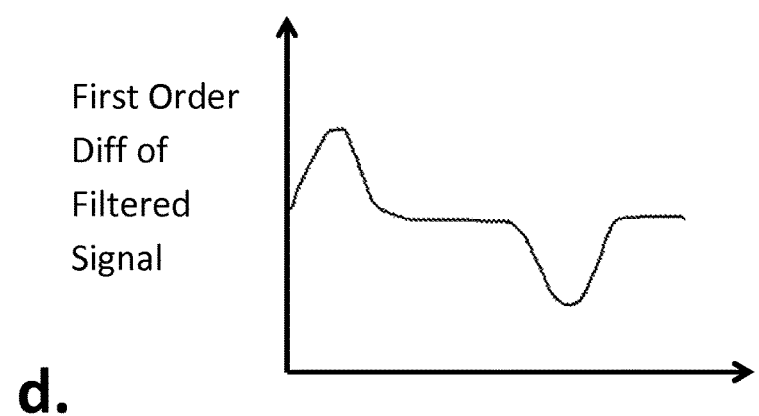
d. First Order Diff of Filtered Signal

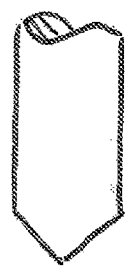  
a.          b.          c.
 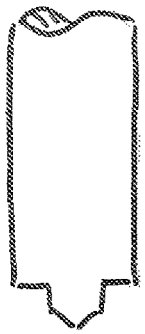 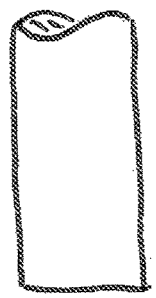
d.          e.          f.
FIG 11.

MEDICAL DEVICE FOR CONTROLLED NAIL PENETRATION

CROSS-REFERENCE TO RELATED APPLICATION

None.

BACKGROUND TO THE PRESENT INVENTION

The present invention relates to a device for controlled penetration of the nail found on the hands and feet of a patient, and more particularly a device for the controlled penetration of the nail to aid in the treatment of infection of the nail such as for example the treatment for Onychomycosis commonly known as fungal nail. The device will penetrate the nail using a cutter advanced by a control system that will prevent the cutter from overrunning and entering the nail bed below.

Onychomycosis is an example of a fungal nail infection that is most common in the feet of the elderly affecting as many as 60% in the United States. It causes the nail to change shape, thicken and becoming brittle. Over the counter creams and ointments have a very low level of efficacy (of between 5-12%). Oral treatments are much more effective, however they must be taken for 2-3 months and can affect the liver making them contraindicated for some patients. An alternative means of treatment is the use of lasers to treat the infection, however the cost of the equipment and treatment is very high making it unavailable to many patients.

If untreated the nail can be permanently deformed and can have a significant impact upon the patient's quality of life due to the unsightly appearance of the nail and pain when wearing shoes.

To increase the local efficacy of topically applied treatment it is advantageous to deliver the treatment to areas within and below the nail. This greatly increases concentration levels that can be achieved in the nail bed and consequently improves efficacy of the treatment. The matrix is the tissue upon which the nail rests, the part of the nail bed that extends beneath the nail root and contains nerves, lymph and blood vessels. The matrix is responsible for the production of the cells that become the nail plate. The nail plate or body of nail is like hair and skin, made of translucent keratin protein made of amino acids. In the nail it forms a strong flexible material made of several layers of dead, flattened cells. If the nail is perforated then it allows antifungal treatment to be applied directly to the nail bed below the nail, where the infection resides. The challenge with drilling through the nail is to penetrate the nail without piercing the nail bed below. The nail bed is very sensitive and piercing it can cause the patient a lot of pain.

US patent application number 2006/0225757 A1 describes a drill for making a hole in the fingernail or toenail, however there is no provision for preventing the drill from overrunning into the nail bed, other than the skill of the user.

U.S. Pat. No. 6,264,628 B1 describes a device for cutting a notch in the nail. In order to prevent damage to the nail bed, the depth to which the notch is cut is predetermined prior to use. There is no method described for detecting the point at which the cutter breaks through the nail.

US patent application number 2011/0046626 A1 describes a method for drilling through the nail without drilling far into the nail bed. The author describes a method for detecting the point at which the drill breaks through the nail and into the nail bed below by measuring the electrical impedance of the tissue being drilled. The electrical impedance of the material being drilled is measured by using the drill as one electrode and having a second electrode placed on the skin of the patient. A change in impedance between the two electrodes may be used to detect the point at which the drill breaks through the nail and into the nail bed below. At this point however the drill may have progressed further into the nail bed than is desirable.

US patent application number 2010/0145373 A1 describes apparatus for drilling a hole in a nail of a subject. The Author describes a drill control unit configured to 2-60 back and forth motions per second. The apparatus is fed into the nail by the user and is dependent upon the user to ensure that it is not pressed too deeply into the nail bed. The Author describes a control unit configured to stop drilling in response to the force exceeding a threshold force, however the force will fluctuate according to the amount applied by the user.

SUMMARY OF THE PRESENT INVENTION

The present invention provides a device for automatically controlling the drilling through a nail of a human or other animal and also provides a device for automatically controlling the drilling through a tissue of a human or other animal. Optional features of both of these devices are also described.

The present invention also provides a method of automatically controlling the drilling through a nail of a human or other animal. It will be appreciated that the optional features described in relation to the device may be used as optional features of the method of the present invention. The method of the present invention may also be used to drill through tissues other than nails.

The present invention also provides a method of treating a nail infection in a human or other animal.

The devices and methods according to the present invention do not require the user to advance the cutter (i.e. drill bit), but instead utilise a control system that controls the rate at which the cutter is advanced and the force that is applied by the cutter. The control system advances the cutter through the nail whilst monitoring the position of the cutter and automatically stops the cutter from advancing once it breaks through the nail in order to ensure that is does not overrun and enter into the nail bed.

The devices and methods according to the present invention may be used to detectably predict the point at which the drill bit or cutter will break out of the nail and then control it so as to prevent it from entering the nail bed and causing the patient pain.

BRIEF DESCRIPTION OF THE DRAWINGS

Various embodiments of the present invention will now be described, by way of example only, and with reference to the accompanying drawings in which:

FIG. 1 is a schematic illustration of the nail penetration device and a possible method of holding the device against the nail during use.

FIG. 2 is a schematic illustration showing that the device consists of two primary components; 1) a reusable hand-piece non-sterile and 2) detachable single use sterile cutting element.

FIG. 3 is a schematic illustration showing how the device may be used to produce an elongated slot shaped aperture in the nail.

Figure 4:
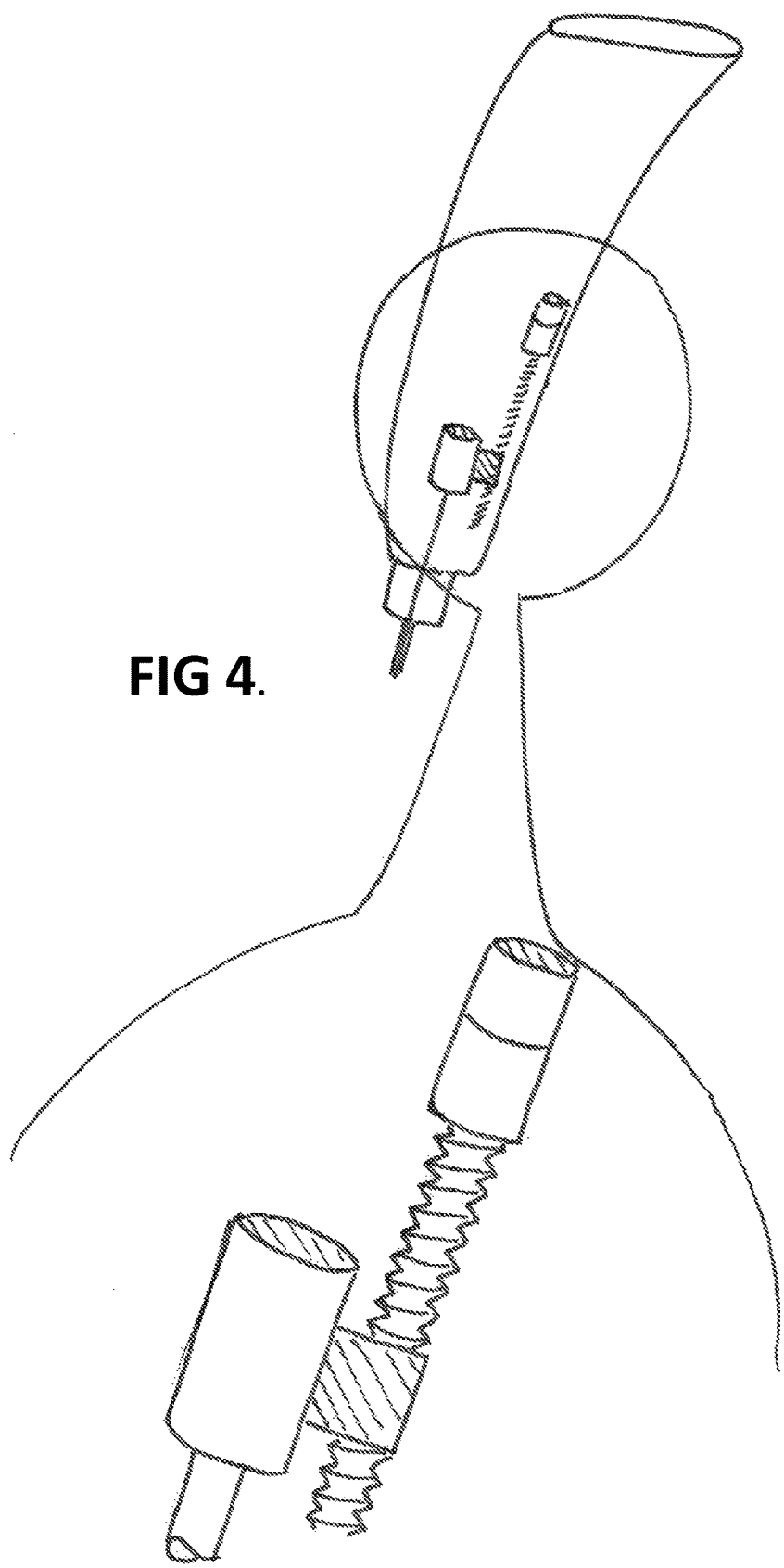
FIG. 4 is a schematic illustration showing a simplified drive mechanism that may be used to advance the cutter in the axial plane during operation (more detail is provided in FIG. 5).

1. A cross-section of the nail
2. The cutter that may take the form of a twist drill, slot cutter, end mill or other appropriate design; possibly including helical or spiral features.
3. Spring used to ensure that the nail is pressed against the nail with sufficient force to ensure reliable operation of the device.
4. A switch or sensor to detect that the spring 3 has been sufficiently compressed.
5. The motor for rotating the cutter possibly also including an integral or separate tachometer for measuring the rotational speed during operation.
6. A component that transfers force between the drive screw for advancing the motor 5 and preventing it from being rotated by the reaction from the cutter 2. A more detailed description is provided in FIG. 7.
7. At least one strain gauge that may be arranged in a Wheatstone Bridge configuration in order to measure axial forces.
8. At least one strain gauge that may be arranged in a Wheatstone Bridge configuration in order to torque or rotational forces.
9. A resistor placed in series for detecting the current flow through the motor 11 used to power the drive mechanism for advancing and retracting the cutter in the axial direction.
10. A resistor placed in series with the motor for detecting the current flow through the motor 5 used to rotate the cutter 2.
11. The motor 11 used to power the drive mechanism for advancing and retracting the cutter in the axial direction.
12. A torque sensor or component used to measure the torque applied to the motor 11 used to power the drive mechanism for advancing and retracting the cutter in the axial direction.
13. The PCB control system used to automate the system and ensure that the cutter does not overrun the nail and enter the nail bed below.

FIG. 6 is a schematic illustration of the nail contacting part of the single use component that will ensure that the device is pressed against the nail with sufficient force to prevent undesirable movement during operation. This also shows the cutter 2 not in contact with the nail 1 at this point.

Figure 5:
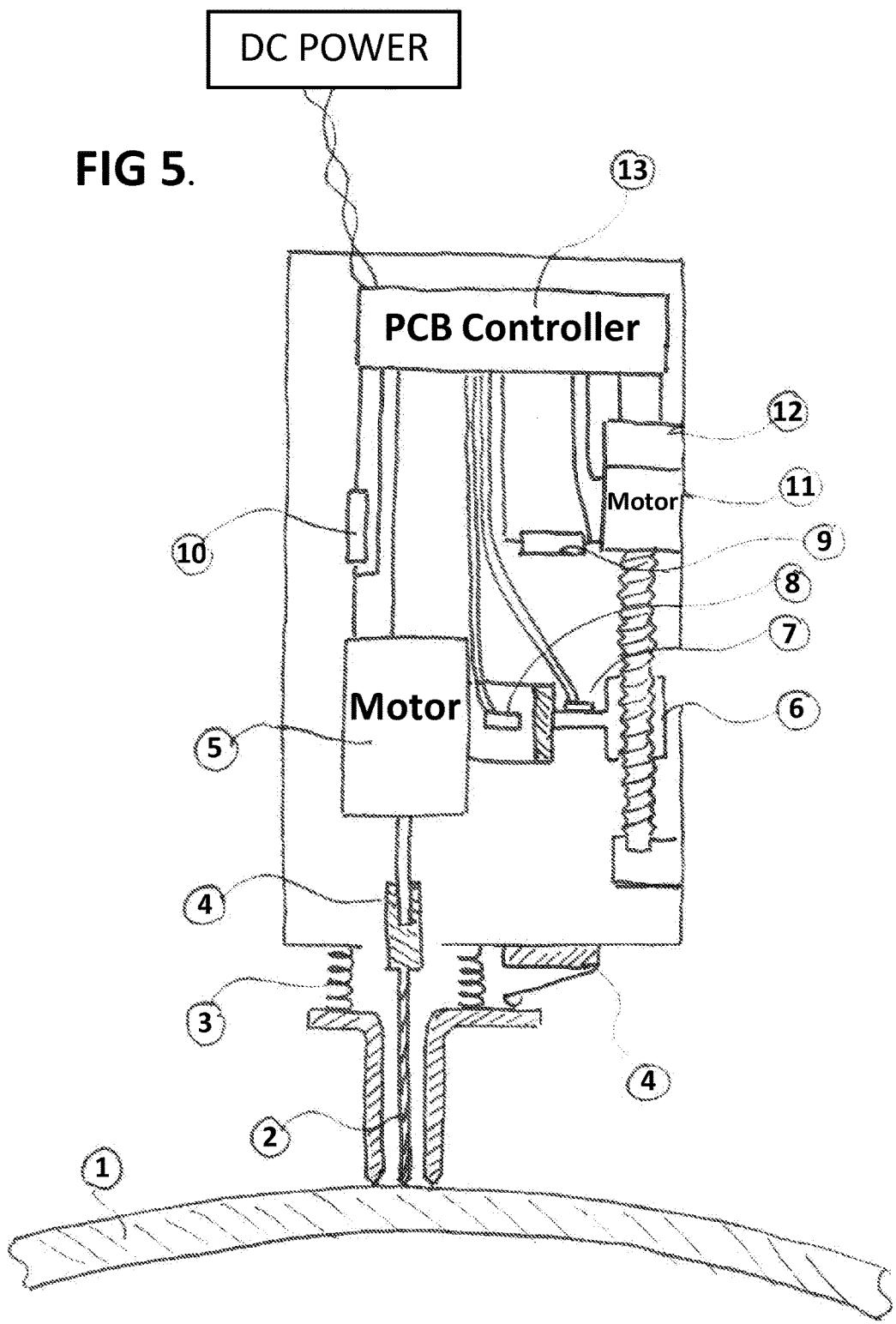
FIG. 5 is a schematic illustration showing an embodiment of the drive mechanism and control system that may be used to advance the cutter in the axial plane and prevent it from overrunning into the nail bed during operation. A numbered components are as follows.

FIG. 7 is a schematic illustration of an embodiment of a component 6 that may be used for one of the proposed methods for measuring the axial force and the torque produced during the cutting process, by using strain gauges 7 and 8 to measure elastic deformation of a component connecting the motor and the drive mechanism shown in FIG. 5.

FIG. 8 is a schematic illustration showing the cutter positioned on a toenail and three distinct stages of operation during use when the cutter is; 1) coming into contact with the nail, 2) passing through the nail, 3) breaking through the nail.

Figure 9:
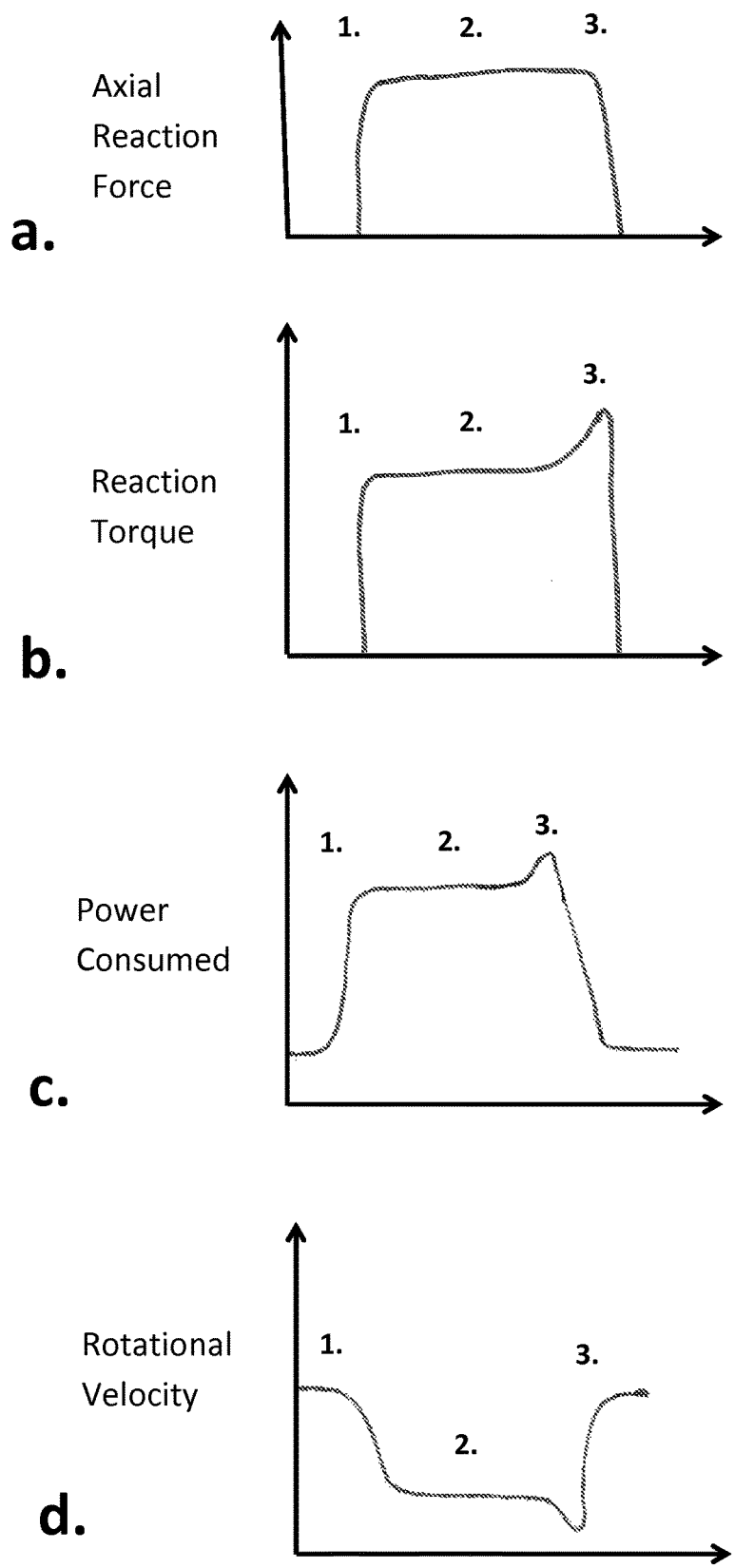

FIG. 9 is a set of illustration of graphs showing the force profiles likely to be seen whilst drilling through a solid material with special reference to features that may be seen during stages 1, 2, and 3 shown in FIG. 8; a) Reaction force on the cutter 2 or motor 5, b) Reaction torque on the cutter 2 or motor 5, c) Power consumed by motor 5, and d) Rotational velocity of the cutter 2.

FIG. 10 is a schematic illustration of graphs showing the how the signals may be filtered including the first-order differential of the signals that may be used to detect the point at which the drill (or cutter 2) breaks through the nail:
a) An unfiltered signal for the force profile
b) The same signal shown in a) filtered using a low-pass filter for example a Kalman filter
c) The first-order differential of an unfiltered signal for the force profile as seen in a)
d) The first-order differential for the filtered signal for the force profile as seen in b)

FIGS. 11a-f is a set of illustration profiles of various cutter design that may be used and that will change the signal profiles shown in FIG. 9:
a) Conventional drill point design, where 50% of the axial force is carried on the leading chisel edge
b) Centre point design similar to a wood drilling bit
c) Circumference cutting design
d) Combination of centre point b) and circumference cutting c) designs
e) Counter bore design designed to produce a counter bore hole
f) Flat end design to help prevent damage to the nail bed when exiting the nail 1.

SUMMARY OF PREFERRED EMBODIMENTS

Reference is now made to FIGS. 1, 2, 4 and 5, of the drawings showing schematic illustrations of an embodiment of the nail penetration device. The device may be handheld and presses against the nail during use as in FIG. 1.

The device may require a predetermined load to be applied, determined by the spring elements 3 shown in FIG. 6, in order to ensure that the device is stable and there is no motion that may prevent the control system from correctly determining the position of the cutter in relation to the surface of the nail.

The device may incorporate a pressure activated switch 4 as in FIG. 5 in order to prevent the device from being operated when not firmly pressed against the nail, where the applied load will help to prevent accidental motion in both the axial and horizontal planes i.e. less likely to slide across the surface of the nail.

The component in FIG. 6, also seen in FIG. 5, helps prevent the likelihood of the device slipping across the surface of the nail.

The device may be either activated by the depression of a button or upon the application of the required amount of load.

The control system may rotate the cutter and advance it into the nail at a constant feed rate until it is halted, e.g. using the drive mechanism 6 shown in FIG. 5 and FIG. 4.

The control system may monitor the progress of the cutter as it is advanced through the nail in order to stop the cutter from advancing as it breaks through the nail thus preventing it from entering the nail bed below.

Various designs of cutter may be used (see some of the possible profiles shown in FIG. 11) in order to make it easier to detect the point at which the cutter breaks through the nail and also reduce the likelihood of unwanted splinters or debris at the point of break out.

The control system may energise the motor in FIG. 4 which rotates the cutter at a suitable rotational speed, for example between 1000 rpm and 100000 rpm.

The control system may energise the lead-screw motor 11 in order to advance the cutter towards the nail 1.

The control system may monitor the progress of the cutter through the nail including stages 1 to 3 depicted in FIG. 8.

The control system may monitor any combination of the following signals in order to determine the progress of the cutter while it is advanced through the nail:—

The axial reaction force experienced by the cutter measured by the strain gauges 7 in FIGS. 5 and 7 or the current flow through the resistor 9 in series with the motor 11 or a drop in speed in motor 11 powering the drive mechanism to advance the cutter in the axial direction; the reaction torque experienced by the cutter measured by the strain gauges 8 in FIGS. 5 and 7 or the current flow through the resistor 10 in series with motor 5 rotating the cutter 6 or the power required to drive the motor rotating the cutter or the change in rotational speed of the cutter and/or the motor rotating the cutter.

The control system may be configured to stop advancing the cutter upon detecting the point at which the cutter breaks through the nail (stage 3 in FIG. 8) by detecting the axial reaction force reducing below a pre-determined threshold as in FIG. 9a.

The control system may be configured to stop advancing the cutter upon detecting the point at which the cutter breaks through the nail (stage 3 in FIG. 8) by detecting the reaction torque reducing below a pre-determined threshold as in FIGS. 9b and c.

The control system may be configured to stop advancing the cutter upon detecting the point at which the cutter breaks through the nail (stage 3 in FIG. 8) by detecting a change in rotational speed of the cutter as in FIG. 9d.

Once the drill bit has cut to the desired depth it may be moved in a translational direction to produce a portal that is longitudinal in form such as a slot as in FIG. 3.

DETAILED DESCRIPTION OF PREFERRED EMBODIMENTS

The present invention relates to a fully automated device that drills through the nail in a controlled manner in order to prevent overrun of the drill 2 into the nail bed below. The device must be held in against the nail 1 (see FIG. 1 and FIG. 6) in a controlled manner in order to accurately track the progress of the cutter 2 through the nail 1 thus preventing it overrunning into the nail bed (see FIG. 8 and FIG. 9). When the device is first placed against the nail 1 the cutter 2 will not be in contact with the nail 1 (see FIG. 6). Upon activation the cutter will start to rotate and will then be advanced in an axial direction towards the nail 1. When the cutter makes contact with the nail 1 there will be a reaction force from the nail 1 in the axial direction and a reaction torque applied to the cutter. These forces can be measured using various sensors, for example; both forces could be measured by using strain gauges 7 and 8 to detect elastic deformation of a component 6 connected indirectly to the cutter as shown in FIG. 5 and FIG. 7. Measuring these forces tells us about the mechanical properties of the material that the cutter 2 is in contact with.

The amount of energy required to rotate the cutter will depend upon the material that the cutter is passing through, i.e. significantly less energy will be required to rotate the cutter whilst it is rotating in free space, when compared to the amount of energy required to rotate the cutter as it is advanced through the nail 1. The amount of energy required to rotate the cutter can be measured (e.g. by measuring the voltage drop across a resistor 10) or controlling the amount of power that is delivered to the motor 5 that drives the cutter. The same principle can also be used in order to measure the amount of energy required to advance the cutter e.g. by measuring the voltage drop across resistor 9 in series with motor 11 it is possible to determine the current drawn by motor 11 and thus determine the axial reaction force generated by the material being drilled. Possibly the simplest way to measure the mechanical properties of the material being drilled would be to measure the current drawn by the motor 5 when rotating the cutter and/or changes in the speed of rotation using a tachometer that is either separate or integral to the motor 5.

As explained in the earlier paragraphs, measuring the forces required to drill through a material provides information about the mechanical properties of the material. As the nail 1 can be considered to be relatively uniform in its mechanical properties we can predict the force profiles that would be obtained by drilling through this material. FIGS. 9a to d shows the force profiles that we would expect to see as the cutter 2 advances through the nail 1. Drilling through a uniform material (such as the nail 1) may be divided into the following three distinct stages (as shown in FIG. 8). As can be seen from FIGS. 9a to d each stage can be identified by features in the force profiles. Stage 1 is when the drill (or cutter 2) starts to enter the material the force profiles rise sharply in line with the increased energy required to rotate the cutter. Stage 2 is while the drill (or cutter 2) is passing through the material and the force profile remains relatively constant. Stage 3 is the point at which the drill (or cutter 2) starts to break out of the material and where a sharp drop in the axial force can be seen. The same is torque also drops sharply once the cutter has broken out of the material, however this is often preceded by an initial increase in torque at the point of breakthrough (see FIGS. 9b, c and a). This information can be used to track the progress of the drill (or cutter 2) through the nail in order to stop the advancement of the drill (or cutter 2) at the point of breakthrough in order to prevent it entering the nail bed below. The nail bed contains lymph and blood vessels and is much softer than the nail which is constructed of primarily keratin. Consequently if the drill (or cutter 2) where to pass through the nail into the nail bed below the system can easily detect a change in the materials being drilled.

The actual signals that may be detected using the methods described in the previous paragraphs may contain noise or fluctuation creating a profile similar to that shown in FIG. 10a. In order to make the system more reliable it may be necessary to filter the signal using a low-pass filter for example a Kalman filter. This will produce a smoother profile similar to the one shown in FIG. 10b.

As stages 1 and 3 are denoted by either a rapid increase or decrease in the forces measured these features may be more easily identified by measuring the first-order differential as in FIG. 10d. The first-order differential may also need to be smoothed using a low pass filter (see FIGS. 10c and d).

There are a number of ways to detect the point at which the drill (or cutter 2) begins to break out of the material including setting a minimum threshold for the forces or the first-order differential of the forces.

Once the system has detected that the drill (or cutter 2) has broken through the material it will stop advancing the drill (or cutter 2) in order to prevent it from penetrating and damaging the nail bed below. At this point the cutter may either be retracted or remain at the same depth and transversely in order to produce a longitudinal slot in the nail (see FIG. 3).

Once a suitable cutter 2 has perforated the nail to produce an access port, a suitable anti-fungal agent (for example a solution containing 1% Terbinafine) can be applied to the nail bed through the access port. The cutter may be used to apply the antifungal agent to the nail bed. If the cutter contains a spiral or helix portion (as in standard twist drill, slot or milling cutter designs) this will facilitate the removal of swarf while cutting. When rotated in the opposite direction the spiral or helix portion may be used to drive (or pump) anti-fungal agent through the nail to the nail bed. A vacuum device may also be incorporated in the device or used in conjunction with the device in order to remove debris that may cause cross-infection.

Reference is now made to FIGS. 8 to 10 which are schematic representations of the stages of the cutter passing through the nail and the signals that may be used and processed in order to detect the point at which the cutter breaks through the nail in order to stop the cutter from advancing into the nail bed.

The axial reaction force may be measured by using strain gauges 7 to detect elastic deformation of a component applying force to advance the cutter as shown in FIG. 5 and FIG. 7.

The axial reaction force may be measured by sensing the level of current required to advance the cutter using the motor 11 for the drive mechanism shown in FIG. 5.

The reaction torque may be measured by strain gauges to detect elastic deformation of a component 12 used to prevent the drive motor 11 for the drive mechanism from rotating as shown in FIG. 5.

The reaction torque may be measured by strain gauges 8 to detect elastic deformation of a component applying used to prevent the drive motor for the cutter from rotating as shown in FIG. 5 and FIG. 7.

The reaction torque may be measured by sensing the level of current required drive the motor 5 that rotates the cutter 2 shown in FIG. 5.

The reaction torque may be measured by sensing the level of power required drive the motor 5 that rotates the cutter 2 shown in FIG.

The reaction torque may be measured by sensing the rotational speed of the motor 5 that rotates the cutter 2 or the cutter itself shown in FIG. 5.

The point at which the cutter breaks through the nail stage 3 in FIG. 8 can be detected by the any of the cutting forces dropping below a threshold that is either pre-determined of calculated from measurements recorded during cutting as in FIGS. 9a to d.

The signals from the various methods of sensing the cutting forces may contain noise or erratic changes, making it difficult to detect the point at which the cutter breaks though the nail as shown in FIGS. 10b and c. In this case a low pass filter may be used to smooth the signal and amplify the feature used to detect the point at which the cutter breaks through the nail see FIGS. 10a and d.

A low pass filter such as a Kalman filter may be used to smooth the signals obtained from various sensors.

The cutter may also cut or mill horizontally in order to produce a slot for example a slot cutter as used in a conventional vertical milling machine. Once the cutter has been advanced to the point of breaking through the nail without overrunning, the cutter can then be moved in a translational direction in order to produce a slot shaped aperture in the nail as in FIG. 3 in order to facilitate better access to the nail bed for antifungal agents used to treat the Onychomycosis.

The invention claimed is:

1. A hand-held nail drill for drilling into a keratinous nail plate of a human or other animal, comprising:
   a body having a proximal end and a distal end;
   a motor for continuously rotating a drill bit about a longitudinal axis in a cutting direction during a keratinous nail plate drilling procedure;
   a keratinous nail plate interface located at the distal end of the body and arranged to allow the drill bit to pass there-through during the keratinous nail plate drilling procedure;
   a drive train for moving the drill bit axially along the longitudinal axis relative to the keratinous nail plate interface;
   a current sensor to detect an amount of energy used by the motor to rotate the drill bit as the drill bit is advanced into the keratinous nail plate, and to output an output signal indicative of the amount of energy used by the motor to rotate the drill bit as the drill bit is advanced into the keratinous nail plate; and
   a control system to receive the output signal of the current sensor and to output a control signal to the drive train to control the drive train and hence the axial rate of movement of the drill bit along the longitudinal axis relative to the keratinous nail plate interface as the drill bit passes into the keratinous nail plate, the control signal being based on comparison of the output signal of the current sensor with an expected profile to prevent the drill bit from advancing into a nailbed underlying the keratinous nail plate;
   wherein the hand-held nail drill is configured such that, in use, the keratinous nail plate interface is configured to maintain the body relative to the keratinous nail plate to prevent movement of the body relative to the keratinous nail plate along the longitudinal axis and to prevent lateral slippage across a top surface of the keratinous nail plate.

2. The hand-held nail drill of claim 1, wherein the amount of energy used by the motor to rotate the drill bit is a function of one or more reaction forces exerted on the drill bit by the drill bit passing into diseased keratinous material of the keratinous nail plate.

3. The hand-held nail drill of claim 2, further comprising a strain gauge associated with the motor for rotating the drill bit, wherein the strain gauge is configured to measure the one or more reaction forces on the drill bit as a function of the change in strain in the strain gauge.

4. The hand-held nail drill of claim 1, wherein the current at sensor is configured to monitor an amount of electrical current supplied to the motor for rotating the drill bit.

5. The hand-held nail drill of claim 1, wherein the control system is configured to control the drive train to axially advance the drill bit at a constant rate along the longitudinal axis relative to the top surface of the keratinous nail plate as the drill bit drills into the keratinous material of the keratinous nail plate.

6. The hand-held nail drill of claim 1, wherein the drill bit has a proximal end connected to the motor for rotating the drill bit and a distal free end, the hand-held nail drill further comprising a second sensor to monitor an axial force exerted on the drill bit in a direction from the distal end to the proximal end.

7. The hand-held nail drill of claim 1, further comprising a strain gauge associated with the motor for rotating the drill bit, wherein the strain gauge is configured to measure the reaction torque acting through the drill bit as a function of the change in strain, wherein the strain gauge is mounted on an elastic or otherwise deformable component connected to the drive train for moving the drill bit or connected to the motor for rotating the drill bit.

8. The hand-held nail drill of claim 1, wherein the control system is configured to reduce the rotational speed of the drill bit, stop rotation of the drill bit, and/or retract the drill bit when the amount of energy stops increasing or starts decreasing.

9. The hand-held nail drill of claim 1, wherein the control system is configured to obtain a first differential of the output signal of the current sensor with respect to time, and wherein the control system is configured to perform one or more of the following when the first differential rises above a threshold or falls below a threshold: reduce the rotational speed of the drill bit; stop rotation of the drill bit; stop advancement of the drill bit; and/or retract the drill bit into the hand-held nail drill.

10. The hand-held nail drill of claim 1, wherein the control system further comprises a low-pass filter for filtering the output signal of the current sensor or for filtering a first order differential of the output signal of the current sensor, and wherein the control system is configured to control the drive train and hence the axial movement of the drill bit based on the filtered signal.

11. The hand-held nail drill of claim 1, wherein the drill bit is removable, the hand-held nail drill further comprising a kit including a plurality of interchangeable drill bits.

12. The hand-held nail drill of claim 1, further comprising a pressure sensor to detect engagement of the keratinous nail plate interface with the keratinous nail plate, and wherein the control system is configured to only allow rotation of the drill bit and/or advancement of the drill bit when engagement is detected.

13. The hand-held nail drill of claim 1, further comprising a guard member surrounding the drill bit and a resilient biasing mechanism configured to resiliently bias the guard member so that the guard member surrounds and extends beyond the free end of the drill bit prior to engagement of the keratinous nail plate interface with the keratinous nail plate.

14. The hand-held nail drill of claim 1, wherein the circumferential surface of the drill bit is a twist drill bit and includes a spiral groove from a distal end of the drill bit towards a shank portion of the drill bit, wherein the control system is configured to control the motor for rotating the drill bit to cause the motor to rotate the drill bit about its longitudinal axis in a first direction for drilling a hole or slot through the keratinous nail plate and to cause the motor to rotate the drill bit about its longitudinal axis in the opposite direction for using the spiral groove to convey a fluid down the drill bit towards its free end and thus through the hole or slot in the keratinous nail plate.

15. A hand-held nail drill for drilling into a keratinous nail plate of a human or other animal, comprising:
a body having a proximal end and a distal end;
a motor for continuously rotating a drill bit about a longitudinal axis in a cutting direction during a keratinous nail plate drilling procedure;
a keratinous nail plate interface located at the distal end of the body and arranged to allow the drill bit to pass there-through during the keratinous nail plate drilling procedure;
a drive train for moving the drill bit axially along the longitudinal axis relative to the keratinous nail plate interface;
at least one sensor configured to monitor an amount of energy required by the motor to rotate the drill bit as the drill bit is advanced into the keratinous nail plate; and
a control system to receive an output signal of the at least one sensor indicative of the amount of energy required by the motor to rotate the drill bit as the drill bit is advanced into the keratinous nail plate and to output a control signal to the drive train to control the drive train and hence the axial rate of movement of the drill bit along the longitudinal axis relative to the keratinous nail plate interface and as the drill bit passes into the keratinous nail plate, the control signal being based on comparison of the output signal of the at least one sensor with an expected profile to prevent the drill bit from advancing into a nailbed underlying the keratinous nail plate;
wherein the hand-held nail drill is configured such that, in use, the keratinous nail plate interface is configured to maintain the body relative to the keratinous nail plate to prevent movement of the body relative to the keratinous nail plate along the longitudinal axis and to prevent lateral slippage across a top surface of the keratinous nail plate;
wherein the drive train comprises a drive train motor for advancing the drill bit axially, the hand-held nail drill further comprising a second sensor to monitor a change in the electrical current supplied to the drive train motor.

16. A hand-held nail drill for drilling into a keratinous nail plate of a human or other animal, comprising:
a body having a proximal end and a distal end;
a motor for continuously rotating a drill bit about a longitudinal axis in a cutting direction during a keratinous nail plate drilling procedure;
a keratinous nail plate interface located at the distal end of the body and arranged to allow the drill bit to pass there-through during the keratinous nail plate drilling procedure;
a drive train for moving the drill bit axially along the longitudinal axis relative to the keratinous nail plate interface;
at least one sensor configured to monitor an amount of energy required by the motor to rotate the drill bit as the drill bit is advanced into the keratinous nail plate; and
a control system to receive an output signal of the at least one sensor indicative of the amount of energy required by the motor to rotate the drill bit as the drill bit is advanced into the keratinous nail plate and to output a control signal to the drive train to control the drive train and hence the axial rate of movement of the drill bit along the longitudinal axis relative to the keratinous nail plate interface and as the drill bit passes into the keratinous nail plate, the control signal being based on comparison of the output signal of the at least one sensor with an expected profile to prevent the drill bit from advancing into a nailbed underlying the keratinous nail plate;
wherein the hand-held nail drill is configured such that, in use, the keratinous nail plate interface is configured to maintain the body relative to the keratinous nail plate to prevent movement of the body relative to the keratinous nail plate along the longitudinal axis and to prevent lateral slippage across a top surface of the keratinous nail plate;
wherein the at least one sensor is configured to monitor the rotational speed of the drill bit directly or indirectly and wherein the control system is configured to control the drive train to axially advance the drill bit until the rotational speed of the drill bit exceeds a threshold value or until the rate of change of the rotational speed exceeds a threshold rate.

17. A hand-held nail drill, comprising:
- a body, having a proximal end and a distal end;
- a drill bit having a longitudinal axis;
- a motor located within the body for rotating the drill bit about the longitudinal axis;
- a keratinous nail plate interface component located at a distal end of the body having an aperture coincident with the longitudinal axis and arranged and dimensioned to allow the drill bit to pass therethrough;
- a drive train within the body for moving the drill bit axially along the longitudinal axis relative to the keratinous nail plate interface component;
- a current sensor configured to output an output signal based on an amount of energy used by the motor to rotate the drill bit during a drilling procedure in which the drill bit is advanced axially through a diseased portion of a keratinous nail plate; and
- a control system to control the drive train, and hence control the axial movement of the drill bit during the drilling procedure, based on the output signal of the current sensor to prevent the drill bit from entering a nailbed underlying the diseased portion of the keratinous nail plate during the drilling procedure;
- wherein the hand-held nail drill is configured such that, in use, the keratinous nail plate interface component abuts a top surface of the keratinous nail plate with sufficient force to grippingly engage therewith to prevent relative movement of the body with respect to the top surface of the keratinous nail plate along the longitudinal axis and in directions transverse thereto.

* * * * *